(12) United States Patent
Thompson et al.

(10) Patent No.: US 7,075,084 B2
(45) Date of Patent: Jul. 11, 2006

(54) ULTRASONIC THERMOGRAPHY INSPECTION METHOD AND APPARATUS

(75) Inventors: Jeffrey G. Thompson, Kent, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 316 days.

(21) Appl. No.: 10/324,014

(22) Filed: Dec. 20, 2002

(65) Prior Publication Data

US 2004/0119019 A1 Jun. 24, 2004

(51) Int. Cl.
*G01N 29/04* (2006.01)

(52) U.S. Cl. .................................... 250/341.6
(58) Field of Classification Search ............. 250/341.6, 250/334, 330; 374/5; 73/584, 602
See application file for complete search history.

(56) References Cited

U.S. PATENT DOCUMENTS

| | | | |
|---|---|---|---|
| 3,648,853 A * | 3/1972 | Winne ...................... | 414/744.3 |
| 4,304,133 A | 12/1981 | Feamster, III ................ | 73/633 |
| 4,841,149 A * | 6/1989 | Martin et al. ................ | 250/330 |
| 4,961,346 A * | 10/1990 | Salvado et al. ................ | 73/644 |
| 5,287,183 A * | 2/1994 | Thomas et al. ............. | 348/571 |
| 5,353,796 A * | 10/1994 | Schroeder et al. .......... | 600/437 |
| 5,404,755 A * | 4/1995 | Olson et al. ................... | 73/639 |
| 5,445,029 A * | 8/1995 | Falsetti et al. ................ | 73/609 |
| 5,634,378 A | 6/1997 | Burkhardt, Jr. et al. . | 74/501.5 R |
| 6,000,844 A | 12/1999 | Cramer et al. ................. | 374/5 |
| 6,190,334 B1 * | 2/2001 | Lasky et al. ................. | 600/587 |
| 6,236,049 B1 | 5/2001 | Thomas et al. .......... | 250/341.6 |
| 6,399,948 B1 | 6/2002 | Thomas et al. .......... | 250/341.6 |
| 6,786,098 B1 * | 9/2004 | Bates .......................... | 73/606 |
| 6,838,670 B1 * | 1/2005 | Lewis et al. ............. | 250/341.6 |
| 2004/0094979 A1 * | 5/2004 | Damhuis ...................... | 294/65 |

FOREIGN PATENT DOCUMENTS

| | | |
|---|---|---|
| DE | 4221486 A1 * | 2/1993 |
| DE | 100 59 854 | 6/2002 |
| JP | 08-062197 | 8/1996 |
| WO | 0153821 | 7/2001 |

\* cited by examiner

*Primary Examiner*—Albert Gagliardi
(74) *Attorney, Agent, or Firm*—Baker & Hostetler LLP

(57) ABSTRACT

A portable thermal imaging analysis for analyzing a specimen includes a frame removably attachable to the specimen by a vacuum and suction cups. The apparatus also includes a sound source and thermal imaging camera that generates thermal images of the specimen along with a controller connected to the sound source and the imaging camera.

14 Claims, 2 Drawing Sheets

ULTRASONIC THERMOGRAPHY INSPECTION METHOD AND APPARATUS

FIELD OF THE INVENTION

The present invention relates to the detection of defects in a material. More particularly, the present invention relates to an apparatus and method for inspecting the structural integrity of certain components, materials and/or structures. The invention is useful in the aviation industry, for example, for field inspections of in-service aircraft fuselages and structural components.

BACKGROUND OF THE INVENTION

Maintaining the structural integrity of certain components and structures is very important in many areas of industry, for example, the aviation and automotive industries, due to safety concerns and the like. Loss of structural integrity can be caused by material defects, such as disbonds, delaminations, cracks, corrosion, inclusions, and/or voids that may exist in the structure or component. For example, it is important in the aviation industry that non-invasive, reliable inspection techniques exist to examine the structural integrity of the aircraft skin, fuselage and structural components of the aircraft to prevent the likelihood that the aircraft does not suffer from structural failure during operation. Therefore a point by point inspection of airplanes is sometimes required. Similarly, by way of example, non-invasive inspection and analysis of the automobile frame components and engine components is also often important. Therefore, non-invasive and non-destructive inspection techniques and methods have been developed and are currently utilized in various industries to analyze and inspect the structural integrity of various materials and components.

One current method for non-invasive analysis of materials and/or components for defects includes treating the material or component with a dye penetrant such that the dye enters any crack or defect that may exist. The component is then cleaned and then treated with a powder that causes the dye remaining in the defects to wick into powder. Next, ultraviolet light is applied to the material or component causing the residual dye remaining in any cracks or defects to fluoresce. This technique has drawbacks however. The dye sometimes is not suitable to identify cracks that located in areas other than the surface of the component. In addition, this technique is can be operator dependent in that the person performing this technique should be adequately trained and skilled.

Other methods currently utilized for the non-invasive analysis and inspection of materials and components include use of an electromagnetic current and use of thermal imaging including ultrasonic excitation or ultrasonic thermography.

The non-invasive analysis method of using an electromagnetic current is carried out by employing an electromagnetic coil to induce eddy currents in the test material or component. The current pattern changes at the location of a defect or crack. This technique requires point by point inspection, which can be labor intensive and is to some extent limited to only specific types of defects. In addition, the evaluator must be properly trained and skilled.

Ultrasonic thermography is a non-invasive analysis method by which a part or portion of a component, material and or structure is "excited" with a high power ultrasonic pulse using an ultrasonic transducer. The resulting vibration of the part under test causes, for example, differential motion across a crack face, producing friction and causing the crack to "heat-up" while the undamaged part of the component is only minimally heated by the ultrasonic waves. The increased heat that diffuses to the surface from the crack causes a local temperature increase that can be detected with an infrared camera. Similarly, the ultrasonic thermography technique can be utilized to identify disbonds and delaminations where the surface temperature above such defects increases due to acoustic damping and again, these areas are located by using an infrared camera.

The ultrasonic thermography technique has been successful for detecting defects in materials and/or components, however current analysis systems employing ultrasonic thermography technique have drawbacks. Some current ultrasonic thermography systems are designed for laboratory use where only small specimens can be analyzed. Therefore those systems are not always well suited for field inspection of materials or components or for inspection of materials that are large in size, for example, fuselages and flight control structures of in-service airplanes. In addition, many of the current ultrasonic thermography systems require manual alignment and placement of the ultrasonic transducer and may not provide a consistent pressure between the traducer and the test surface or part, which can negatively affect the repeatability and accuracy of the technique. Too much or too little pressure may inhibit repeatable detection. In addition, misalignment of the transducer can cause the part or surface being inspected to be cut or burned.

Accordingly, it is desirable to provide a method and apparatus for detecting multiple defect types in both metal and composite structures. It is also desirable to provide an apparatus and method for effectuating the quick and efficient inspection and analysis of large components and/or materials, such as airplane fuselages and structures, in real-time. It is further desirable to provide a repeatable analysis method and apparatus utilizing ultrasonic thermography for effectuating inspection of large components or areas to detect cracks, disbonds, and/or corrosion.

SUMMARY OF THE INVENTION

The foregoing needs are met, at least in part, by the present invention where, in one aspect, a portable thermal imaging analysis apparatus for analyzing a specimen is provided having a frame that removably attaches to the specimen. The apparatus additionally includes a sound source mounted to the frame and a thermal imaging camera for generating thermal images of the specimen. The apparatus also has a controller that is connected to the sound source and the thermal imaging camera.

In accordance with another aspect of the present invention, a portable thermal imaging analysis apparatus for analyzing a specimen is provided having an attaching means that removably attaches to the specimen. The apparatus also includes a sound producing means mounted to the attaching means and a means for generating thermal images of the specimen. The apparatus additionally includes a means for controlling the sound producing means and the means for generating thermal images.

In accordance with yet another aspect of the present invention, a method for analyzing a specimen is provided comprising the steps of: attaching a frame to the specimen that supports a sound source; emitting a sound signal onto the specimen with the sound source; and generating a thermal image of the specimen.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

The present invention provides an ultrasonic thermography apparatus and method for analyzing and inspecting the structural integrity of metal and composite structures. The preferred embodiment is particularly suitable for use in conjunction with airplanes and is suitable for inspecting in-service airplanes for defects such as disbonds, delaminations, cracks and corrosion. It should be understood, however, that the present invention is not limited in its use with airplane but, for example, can be used for the inspection and analysis of automobiles or other structures.

Figure 1:
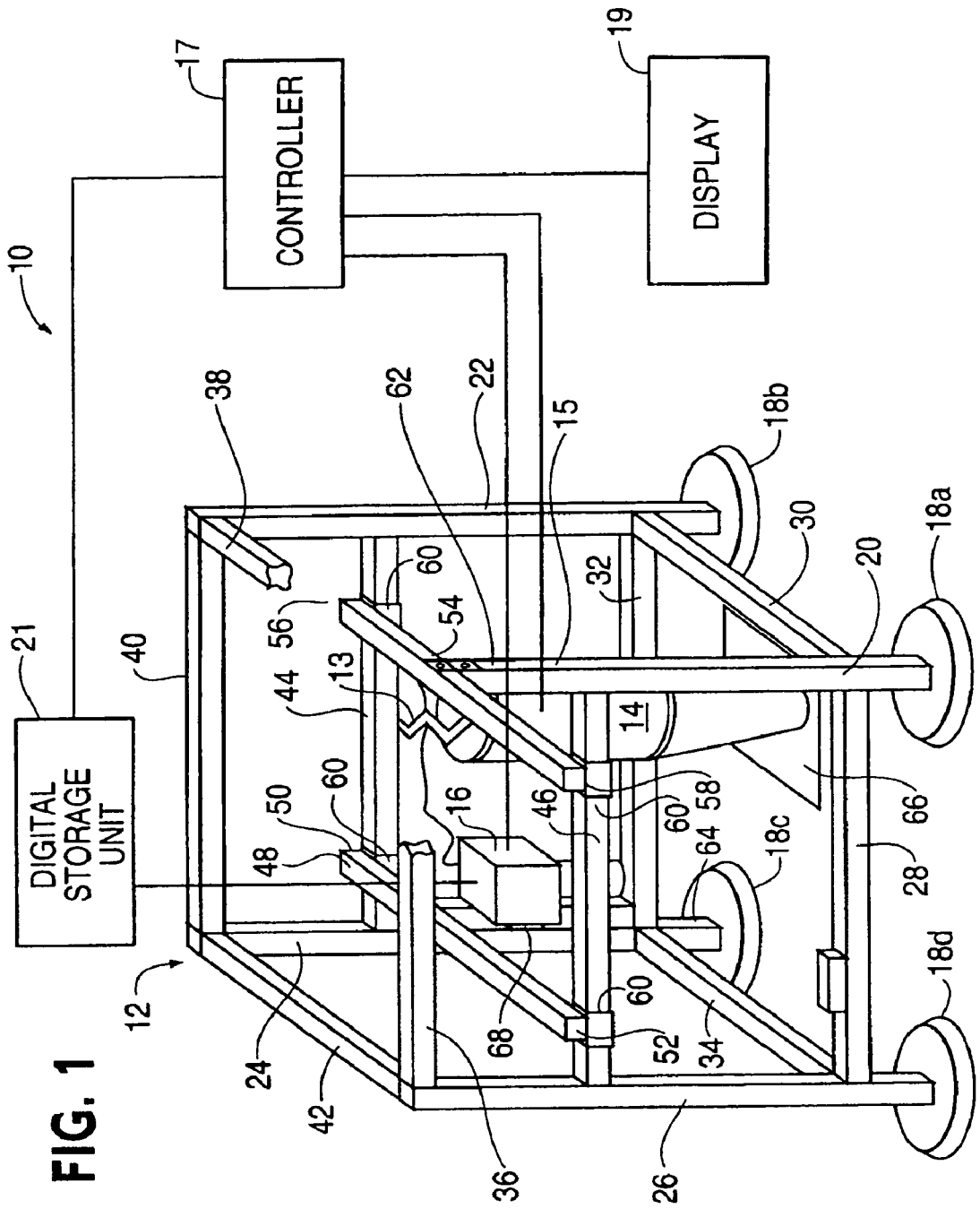
FIG. 1 is an illustration of an ultrasonic thermography inspection apparatus in accordance with a preferred embodiment of the present invention, showing a partially perspective view and a partially block diagram view.

Referring now to the figures, wherein like reference numerals indicate like elements, FIG. 1 shows a partial perspective view of an ultrasonic thermography inspection apparatus 10, in accordance with an embodiment of the present invention. The ultrasonic thermography inspection apparatus 10 includes a frame 12 having multiple frame members, a biasing element 13, a sound source, preferably an ultrasonic transducer 14 connected to an actuator 15, a thermal imaging camera 16 and a system controller 17. The apparatus 10 further includes a pneumatic actuator and vacuum attachment assembly (See FIG. 2) that includes the actuator 15 and four vacuum cups 18a, 18b, 18c and 18d that are attached to the frame 12. The system controller 17 can have an associated display 19.

As depicted in FIG. 1, the frame 12 preferably includes four vertical frame members 20, 22, 24 and 26 to which the vacuum cups 18a, 18b, 18c 18d are attached. The frame 12 additionally includes lower transverse frame members 28, 30, 32, 34. Lower transverse frame member 28 extends between and is attached to vertical frame members 26 and 20. Lower transverse frame member 30 extends between and is attached to vertical frame members 20 and 22. Lower transverse frame member 32 extends between and is attached to vertical frame members 22 and 24. And lower transverse frame member 34 extends between and is attached to vertical frame members 24 and 26. The frame 12 also includes upper transverse frame members 36, 38, 40, 42 that are coupled to and extend between the vertical frame members 20, 22, 24, 26. Upper transverse frame member 36 extends between and is attached to vertical frame members 20 and 26. Upper transverse frame member 38 extends between and is attached to vertical frame members 20 and 22. Upper transverse frame member 40 extends between and is attached to vertical frame members 22 and 24. Upper transverse frame member 42 extends between and is attached to vertical frame members 24 and 26.

The frame 12 of the apparatus 10 additionally includes a first cross bar 44 that is attached to and extends between vertical frame members 22 and 24 and a second cross bar 46 that is attached to and extends between vertical frame members 20 and 26. The frame 12 has a first slider bar 48 having a first end 50 slidably coupled to the first cross bar 44 and a second end 52 slidably coupled to the second cross bar 46 such that it can translate back and forth between vertical frame members 20, 22 and members 24, 26. The frame 12 also has a second slider bar 54 having a first end 56 slidably coupled to the first cross bar 44 and a second end 58 slidably coupled to the second cross bar 46 such that it can translate back and forth between vertical frame members 20, 22 and members 24, 26.

The slider bars 48, 54 are preferably coupled to the cross bars 44, 46 via linear bearings 60 or other suitable slidable coupling means known in the art that can enable it to slide along cross bars 44 and 46.

The actuator 15 is attached to a vertical holder bar 62 that is slidably coupled to the second slider bar 54. The vertical holder bar 62 is preferably rigidly attached to the holder bar 62 via mechanical attachment means such as bolt and/or clamp. Alternatively, the vertical holder may be coupled to the slider bar 54 via linear bearing or other suitable slidable coupling means known in the art such that it can translate between cross bars 44 and 46. Similarly, as depicted in FIG. 1, the thermal imaging camera 16 is adjustably mounted to the second vertical holder bar 68. The vertical holder bar 68 is rigidly attached to the holder bar 62 via mechanical attachment such as a bolt and/or clamp first slider bar 48. Alternatively, the vertical holder 68 may be coupled to the slider bar 48 via linear bearing or other suitable slidable coupling means known in the art such that it can translate between cross bars 44 and 46.

Figure 2:
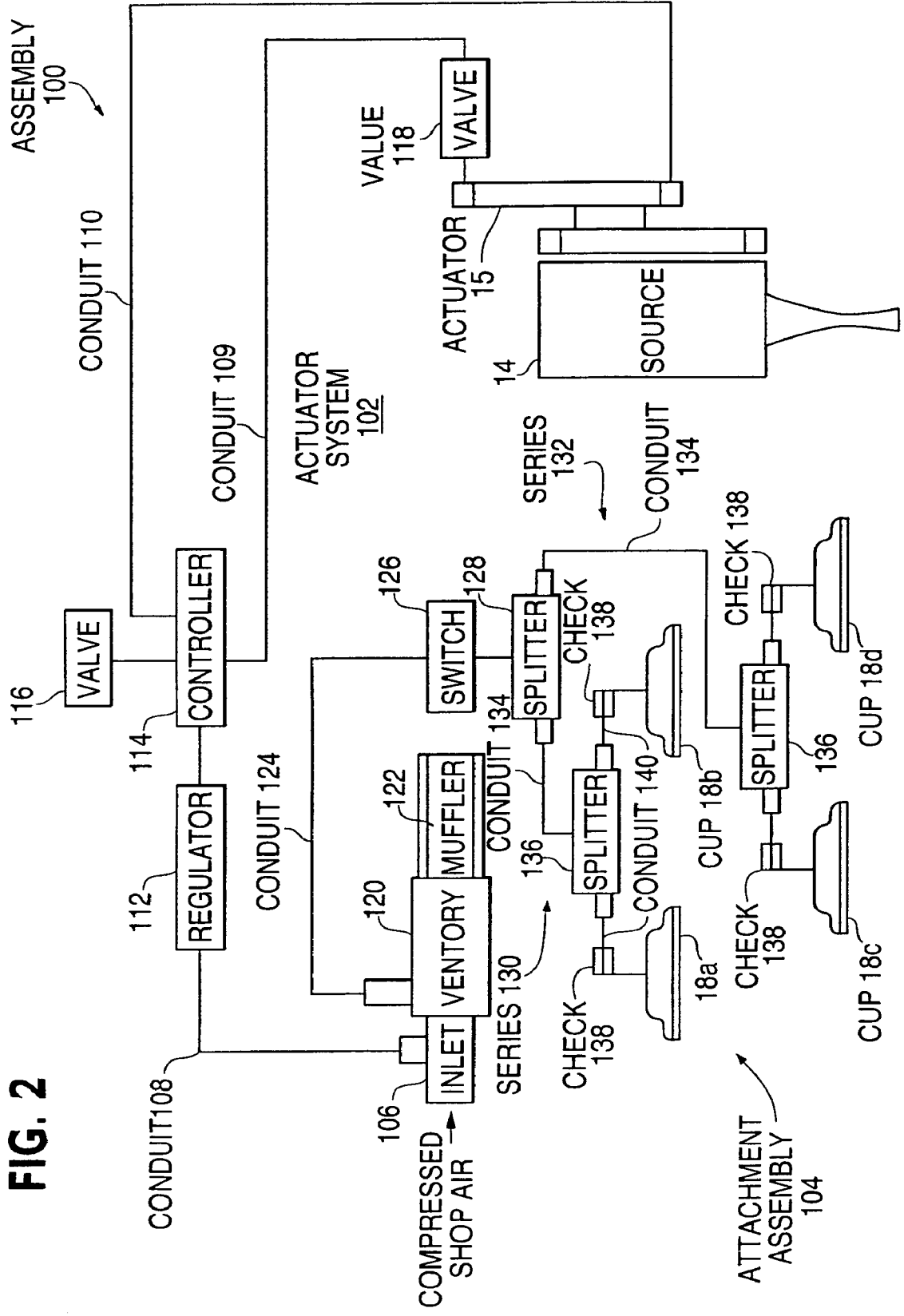
FIG. 2 is a schematic view of a pneumatic assembly utilized in a preferred embodiment of the present invention.

Referring now to FIGS. 1 and 2, the sound source 14 is preferably an ultrasonic transducer attached to the actuator 15. The transducer 14 preferably includes a piezoelectric element that generates ultrasonic energy within a desired ultrasonic or sonic frequency band for a certain length of time. The transducer 14 can be any transducer capable of generating ultrasonic energy preferably at varying ultrasonic frequencies, power levels and pulse durations. As depicted in FIG. 1, the biasing element 13 is preferably a spring that attaches to and extends between one of the upper frame members 36, 38, 40, 42 and the ultrasonic transducer 14. The spring 13 biases the transducer 14 in the downward direction or in the direction of the specimen to be analyzed. The spring 13 provides adjustable pre-load force between the ultrasonic transducer 14 and the specimen during attachment of the apparatus to the specimen. The pre-load force provided by the spring 13 is less than the suctioned force generated by the vacuum cups 18a, 18b, 18c, 18d allowing the transducer to translate in the upward direction or direction away from the specimen during attachment.

As depicted in FIG. 1, the ultrasonic energy from the transducer 14 can be coupled to a specimen, part or area to be tested through a coupler 66. The coupler 66 is a mechanical contact that is in contact with both the ultrasonic transducer 14 and the specimen. The coupler 66 is preferably a thin piece of soft metal, such as copper, that effectively couples the ultrasonic energy to the specimen. Alternatively, other materials known in the art other than copper may be used, for example, any material that is soft and malleable that can be deformed against the end of the transducer and prevent the transducer from bouncing and/or sliding along the specimen during operation. Alternatively, various applications, such as the analysis of composite materials, may not require the use of a coupler 66.

The actuator 15 is preferably a linear stroke, double action pneumatic actuator 15 that functions to translate the ultrasonic transducer 14 in a generally upward and downward direction with respect to the specimen. The pneumatic actuator 15 can be powered by compressed and/or pressured air and translates the ultrasonic transducer 14 such that the transducer 14 preferably applies approximately 10 lbs. to approximately 25 lbs. of pressure on the test surface or test part. More preferably, the actuator 15 exerts approximately 15 lbs. to approximately 20 lbs. of pressure. Use of the actuator 15 enables the analysis method herein described to be repeated and provides a consistent placement of the transducer 14 against the specimen and/or coupler.

The actuator can be any actuator suitable for the purposes described herein, for example, the actuation need not be pneumatic and the actuator may provide more or less than the prescribed 10 to 25 lbs. of pressure Referring now to FIG. 2, a pneumatic assembly 100 employed in an embodiment of the present invention to power the pneumatic actuator 15 and vacuum cups 18a, 18b, 18c, 18d is schematically depicted. The assembly 100 is preferably a parallel system that includes the actuator system, generally designated 102, and an attachment assembly, generally designated 104. Each system, 102, 104 has a common compressed or pressured air inlet 106 where the pressurized air enters the pneumatic assembly 100.

As depicted in FIG. 2, the actuator system 102 has an air inlet conduit 108 for carrying pressurized air from the inlet 106 to the actuator system 102. The actuator system 102 further includes air conduits 109 and 110 which function to carry pressurized air to and from the actuator 15 during operation. The actuator system 102 also includes an air regulator 112, a controller 114, a first air control valve 116 and second air control valve 118.

The controller 114 is preferably a two position, four way spool valve that is toggle activated that controls the up and down movements of the actuator 15. Alternative controllers may also be utilized. When the controller 114 is in a first position, it pressurizes the air conduit 109 while it vents air conduit 110, causing the actuator 15 to translate the transducer 14 in the direction towards the specimen and contact the specimen. In this position, the first air control valve 116 functions to adjust the air pressure provided to the actuator 15, controlling the movement of the actuator 15 and transducer 14 toward the specimen. It also senses the pressure being exerted by the transducer 14 on the specimen and regulates the pressure being applied to specimen by the ultrasonic transducer 14.

Alternatively, when the controller 114 is in a second position, it pressurizes the air conduit 110 while it vents air conduit 109, causing the actuator 15 to translate the transducer 14 in the upward direction away from the specimen. In this position, the second air control valve 118 functions to adjust the air pressure provided to the actuator, controlling the movement of the actuator 15 and transducer 14 away from the specimen.

The air regulator 112, controller 114, first control valve 116 and second control valve 118 combine to control the amount of compressed air powering the actuator 15, in turn controlling the translation of the ultrasonic actuator 14, thereby controlling the distance at which the ultrasonic transducer 14 is positioned with respect to the specimen. In addition, the aforementioned components also combine to control the amount of pressure applied to the specimen by the transducer 14 via the actuator 15. The apparatus 10 is generally preferably arranged so that the actuator 15 moves the transducer 14 vertically downwards toward the specimen. However, other orientations are possible.

As illustrated in FIG. 2, the attachment assembly 104 is a vacuum attachment assembly having a venturi 120 coupled to the air inlet 106. The venturi 120 includes an exhaust muffler 122. The attachment assembly 104 also includes a vacuum conduit 124, a vacuum switch 126 and a two-way splitter 128 that splits the vacuum conduit 126 into two vacuum cup series, generally designated 130 and 132. Each of the series 130, 132 include two of the vacuum cups 18a, 18b, 18c, 18d. Alternative embodiments covered by the present invention may include more or less vacuum cups coupled to one another in multiple series or in a single series.

Each vacuum cup series 130, 132 includes a vacuum air conduit 134, a two-way splitter 136, a pair of check valves 138 and a pair of air conduits 140. The conduit 134 provides the vacuum suction to the two-way splitter 136 which splits the conduit and provides suction the assemblies' 130, 132 and their respective vacuum cups via the conduits 140 and the check valves 138. The check valves 138 allow vacuum air to be provided to individual vacuum cups 18a, 18b, 18c, 18d or removed from individual vacuum cups 18a, 18b, 18c, 18d whereas the switch 126 functions to turn the vacuum air "on" or "off" in the entire attachment assembly 104.

During operation, compressed air from the inlet 106 enters the venturi 120 and exits the exhaust 122, creating a vacuum. When the vacuum switch 126 is in the "on" position, vacuum air is provided to the vacuum cups 18a, 18b, 18c, 18d via the above described conduits, splitters and check valve components, enabling the apparatus 10 to be attached to the specimen, part and/or component to be analyzed. Alternatively, when the vacuum switch 126 is in the "off" position, vacuum air is not provided to the vacuum cups 18a, 18b, 18c, 18d and the apparatus cannot be attached to the specimen, etc.

As illustrated in FIG. 1, the thermal imaging camera 16 is preferably an infrared camera that generates images of the specimen, part or area being tested in association with ultrasonic excitations of the test specimen, part or area. In addition, the infrared camera 16 can convert the heat energy detected to grayscale information if desired. The images and grayscale information are preferably displayed on the image display 19. The image information is captured preferably by using a digital storage unit 21, located within the apparatus 10 or located remotely and accessed electronically. Preferably, digital storage unit 21 allows for the infrared images to be recorded digitally and/or by standard video, depending upon application and the size of the defect.

Alternatively, the image data and grayscale data may stored in databases located within the ultrasonic thermography inspection apparatus 10, located within storage media or located remotely. The remotely located databases can be accessible by corded and/or wireless communication including the Internet, Ethernet, or other remote memory storage facility. The storage media upon which the image and grayscale information is stored can include, but is not limited to, floppy disc (including ZIP); tape drive cartridge (such as DAT); optical media (such as CD-ROM, DVD-ROM, etc.); flash memory (such as smart media, compact flash, PC card memory, memory sticks, flash SIMMs and DIMMS, etc.); magnetic based media, magneto optical; USB drives; Nanotechnology memory or any other storage media that an operator can store or retrieve information from it. A person skilled in the art will recognize that any suitable storage media can be used.

As previously described, the infrared camera 16 is mounted to the vertical holder bar 64 that extends from the slider bar 48. The infrared camera 16 is preferably mounted to the vertical holder bar 64 via linear bearing or other suitable coupling means known in the art such that the camera 16, enabling it to be positioned at varying distances from the specimen, test part or area. The aforementioned positioning of the infrared camera allows the camera 16 to move along a X, Y and Z axis, allowing the camera to be positioned at multiple locations with respect to the part or area being tested.

The system controller 17 may be disposed within the frame 12 where it directly communicates with the ultrasonic transducer 15 and thermal imaging camera 16 via wires. The system controller 17 can be any computer suitable for carrying out the analysis process described herein. Alternatively, the controller 17, may be remotely located away from the apparatus 10 and communicate in either a corded or wireless fashion with the camera 16 and ultrasonic transducer 15. Similarly, the image and grayscale data may be stored locally on the unit on a hard drive, compact disc, other storage media or may be stored remotely via corded or wireless communication.

During operation, analysis and/or inspection is initiated by first attaching the ultrasonic thermography apparatus 10 to the specimen to be analyzed by switching the previously described vacuum switch 126 "on," activating the attachment apparatus 104. Next, a baseline image of the test area is taken by the infrared camera 16 and stored in the digital storage unit 21 or other storage media previously described, providing a reference point for analysis. The ultrasonic transducer 14 is then positioned and adjusted such that it is held in contact with the test surface using the pneumatic actuator 15 and controller 114, providing proper pressure between the specimen and/or coupler 66 and the transducer 14.

Also during operation, the system controller 17 provides timing between the transducer 14 and the infrared camera 16. Once the analysis process is initiated, the controller 17 causes the camera 16 to begin taking sequential images of the specimen, test part or area at a predetermined rate. Once the image sequence begins, the controller 17 sends a signal to the transducer 14 to generate the ultrasonic signal. The ultrasonic energy is in the form of a pulse at a predetermined frequency. The pulse time periods and frequencies and input power of the apparatus 10 can vary depending on the apparatus being used and the composition of the area or part being tested.

Upon application of the ultrasonic energy, the specimen becomes "excited" and the areas of the test area that contain defects vibrate with greater amplitude and cause the surface to heat up, which is detected by the camera 16 and can be viewed on the display and/or stored. The camera 16 may also convert the heat energy images is to grayscale information. The grayscale information is then sent to the display and/or stored for later review and analysis. If the grayscale level of the test area during the application of ultrasonic energy exceeds the baseline threshold level previously recorded, the peak store image capture unit records and retains this new level on the image display, immediately notifying the operator of the existence of defects. The above-described process may now be repeated on the same area or the apparatus may be transferred to a new area to be tested.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A portable thermal imaging analysis apparatus for analyzing an airplane, comprising:
   a frame that removably attaches to the airplane;
   a sound source mounted to the frame;
   a connector for attaching to a supply of compressed air;
   an actuator in fluid communication with the connector, the actuator being powered by the supply of compressed air and controlled to urge the sound source towards the airplane;
   a vacuum generator being in fluid communication with the connector, the vacuum generator being configured to generate a partial vacuum in response to the supply of compressed air;
   a plurality of suction cups attached to the frame and configured to releasably attach the frame to the airplane, the plurality of suction cups being in fluid communication with the vacuum generator;
   a thermal imaging camera for generating thermal images of the airplane; and
   a controller connected to said sound source and said thermal imaging camera.

2. The portable thermal imaging analysis apparatus according to claim 1, wherein said sound source is mounted to said frame via an actuator mounted to said frame that moves said sound source towards and away from the airplane.

3. The portable thermal imaging analysis apparatus according to claim 2, wherein said actuator moves said sound source into contact with the airplane.

4. The portable thermal imaging analysis apparatus according to claim 3, wherein said actuator moves said sound source into contact with the airplane with approximately 10 pounds of pressure to approximately 25 pounds of pressure.

5. The portable thermal imaging analysis apparatus according to claim 3, wherein said actuator moves said sound source into contact with the airplane with approximately 15 pounds of pressure to approximately 20 pounds of pressure.

6. The portable thermal imaging analysis apparatus according to claim 1, wherein said sound source is an ultrasonic transducer.

7. The portable thermal imaging analysis apparatus according to claim 1, further comprising a coupler between said sound source and the airplane, providing contact between said sound source and the airplane.

8. The portable thermal imaging analysis apparatus according to claim 1, wherein thermal imaging camera is pivotably mounted on said frame for movement relative to the airplane.

9. The portable thermal imaging analysis apparatus according to claim 1, wherein said vacuum generator comprises: a venturi connected to said supply of compressed air, said venturi having a vacuum output port; and at least one suction cup connected to the vacuum outlet port by a conduit.

10. A portable thermal imaging analysis apparatus for analyzing an airplane, comprising:
   attaching means removably attaching to the airplane;
   sound producing means mounted to the attaching means;
   connecting means for attaching to a supply of compressed air;
   pneumatic actuating means powered by the supply of compressed air and in fluid communication with the connecting means, the pneumatic actuating means being configured to urge the sound producing means towards the airplane;
   vacuum generating means in fluid communication with the connecting means and the attaching means, wherein vacuum generated by the vacuum generating means in response to the supply of compressed air removably attaches the attaching means to the airplane;
   means for generating thermal images of the airplane; and
   means for controlling the sound producing means and the means for generating thermal images.

11. The portable thermal imaging analysis apparatus according to claim 10, wherein said actuating means moves said sound producing means towards and away from the airplane.

12. The portable thermal imaging analysis apparatus according to claim 11, wherein said actuating means moves said sound producing means into contact with the airplane.

13. The portable thermal imaging analysis apparatus according to claim 10, further comprising a means for coupling said sound producing means and the airplane, providing contact between said sound producing means and the airplane.

14. A method for analyzing an airplane comprising the steps of:
   removably attaching a frame to the airplane that supports a sound source;
   connecting a supply of compressed air to the frame;
   urging the sound source towards the specimen in response to the supply of compressed air;
   generating a partial vacuum in response to the supply of compressed air, wherein the partial vacuum is utilized to removably attach the frame to the airplane;
   emitting a sound signal onto the airplane with the sound source; and
   generating a thermal image of the airplane.

* * * * *